United States Patent [19]

Romandi

[11] Patent Number: 5,081,543

[45] Date of Patent: Jan. 14, 1992

[54] MEDICAL DIAGNOSTICS INSTALLATION WITH MULTIPLE, WIRELESS CONTROL SIGNAL TRANSMISSION CHANNELS

[75] Inventor: Denes Romandi, Erlangen, Fed. Rep. of Germany

[73] Assignee: Siemens Aktiengesellschaft, Munich, Fed. Rep. of Germany

[21] Appl. No.: 627,253

[22] Filed: Dec. 14, 1990

[30] Foreign Application Priority Data

Jan. 12, 1990 [EP] European Pat. Off. ......... 90100648.6

[51] Int. Cl.⁵ .............................................. H04B 10/00
[52] U.S. Cl. ..................................... 359/145; 359/161
[58] Field of Search ............... 455/603, 612, 607, 66; 359/145, 161

[56] References Cited

U.S. PATENT DOCUMENTS

| | | | |
|---|---|---|---|
| 4,426,738 | 1/1984 | Sato | 455/603 |
| 4,837,857 | 6/1989 | Scheller | 455/603 |
| 4,887,313 | 12/1989 | Luke | 455/612 |
| 4,904,993 | 2/1990 | Sato | 455/603 |
| 4,965,856 | 11/1990 | Swanic | 455/617 |

FOREIGN PATENT DOCUMENTS 0338765 10/1989 European Pat. Off. ............ 455/617
3036217 4/1982 Fed. Rep. of Germany .

OTHER PUBLICATIONS

Patent Abstracts of Japan, vol. 11, No. 170 (P-581), Jun. 1987, Publication No. 62002183.
"Ultrasonic/Infrared Barrier", Elektor No. 1983, pp. 1158, 1159.

Primary Examiner—Reinhard J. Eisenzopf
Assistant Examiner—L. Pascal

[57] ABSTRACT

A medical diagnostics installation has an examination station at which a patient and medical examination equipment are disposed, and a control console disposed remotely therefrom. At least two different wireless control signal transmission channels are provided, each sending control signals to the examination station simultaneously by means of different types of information-carrying signals, such as an ultrasound signal and an infrared signal. Since the different types of information-carrying signals are affected by respectively different types of disturbances in the transmission path, the risk of an incoming control signal being misinterpreted due to the presence of a degraded signal is minimized.

2 Claims, 1 Drawing Sheet

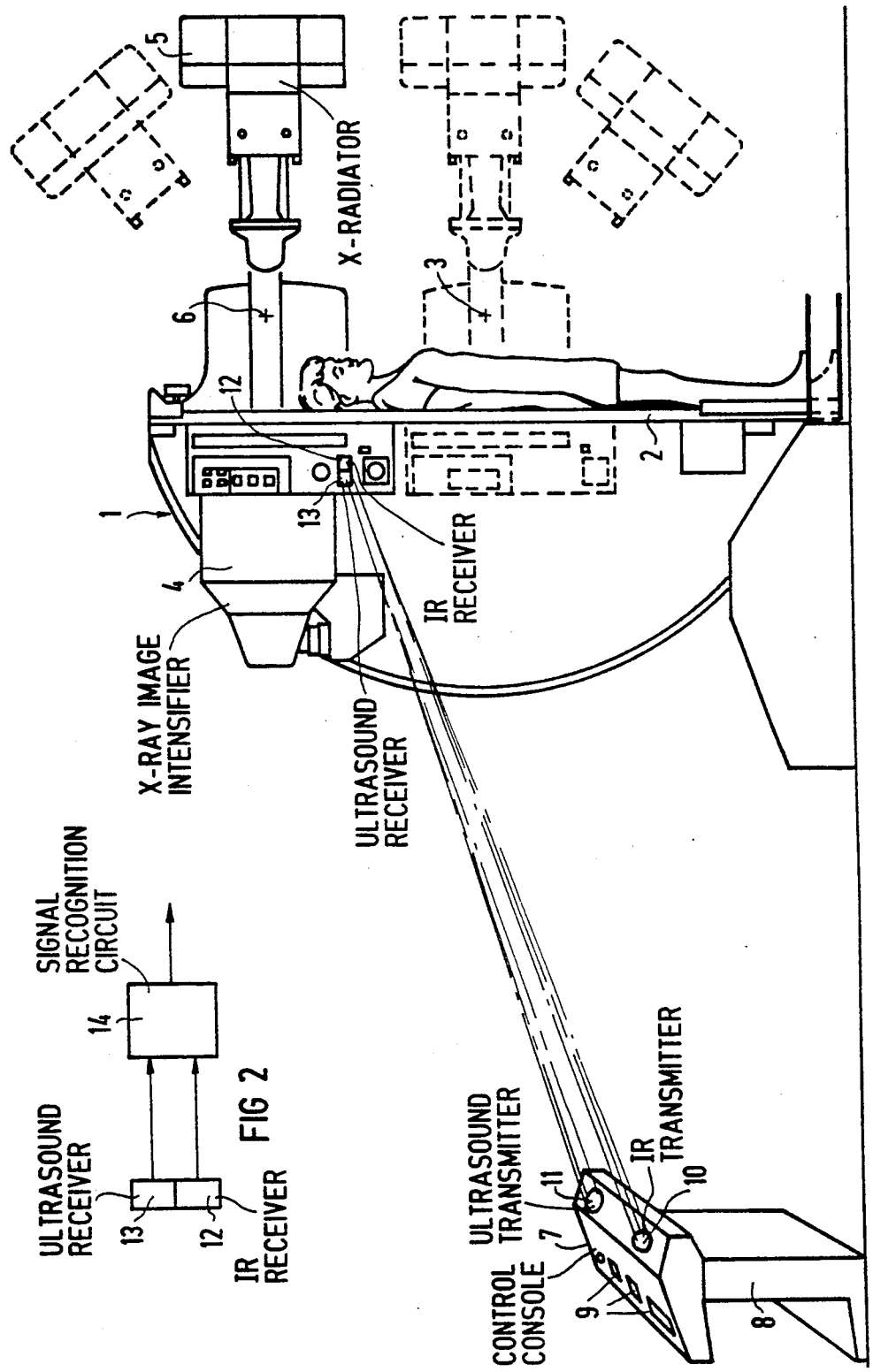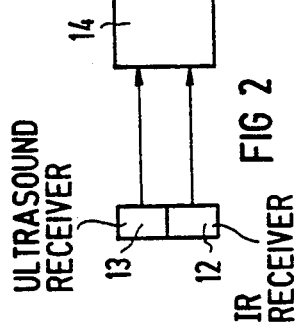

MEDICAL DIAGNOSTICS INSTALLATION WITH MULTIPLE, WIRELESS CONTROL SIGNAL TRANSMISSION CHANNELS

BACKGROUND OF THE INVENTION

1. Field of the Invention

The present invention is directed to installations for conducting medical examinations, and in particular to a system for supplying control signals to an examination apparatus from a control console located remotely therefrom.

2. Description of the Prior Art

It is known in medical technology to transmit information by means of cables or light waveguides. It is known, for example, to remotely control x-ray examination equipment in this manner. It is also known to transmit signals from the radiation detector in an automatic exposure unit to an allocated circuit by this manner, as well as to trigger the generation of radiation and the monitoring of radiation by such remote transmission. Fixed wiring in the form floor cables constitutes an impediment to operating personnel, and installing such cables in the walls, floor or ceiling of the examination room adds to the cost of the installation and can present difficulties in obtaining access to the cables for maintenance. Moreover, fixed wiring is sensitive to electrical disturbances which can degrade the signals carried thereby. Theoretically, therefore, it would be preferable to operate the components of a medical diagnostics installation by wireless remote control.

Wireless remote control using infrared or ultrasound signals is known, for example, in entertainment electronics. The use of such wireless remote control in medical technology has been cautiously approached, because both types of transmission can be disturbed, thereby resulting in the receipt of an incorrect control signal. Infrared radiation, for example, can be disturbed by radiation components in the spectrum of fluorescent tubes, and ultrasound emission can be disturbed by spectral components in room noises.

SUMMARY OF THE INVENTION

It is an object of the present invention to provide a medical technology diagnostics installation having at least one remotely controllable medical technology component wherein action of the controllable component based on an incorrectly received control signal is prevented.

The above object is achieved in a medical diagnostics installation with a control console disposed remote from an examination station at which at least one controllable component is located, and wherein transmission of the control instructions ensues simultaneously via two different wireless transmission channels, each channel transmitting a different type of information-carrying signal. For example, one transmission channel may be an infrared transmission channel and the other transmission channel may be an ultrasound emission channel. The signals received via the two different channels are supplied to a recognition circuit at the examination station, and execution of the control instruction is undertaken at the examination station only when the information simultaneously received via the infrared channel and the ultrasound channel are identical. If disturbances occur in either of the infrared transmission path or the ultrasound transmission path such that the received signals do not match, execution of the control instruction is prevented. The probability that both channels will be simultaneously disturbed in the same way is negligibly low.

The apparatus disclosed herein provides a simple, mobile and highly reliable transmission connection between the control console and a wirelessly remote-controlled component at the examination station.

DESCRIPTION OF THE DRAWINGS

FIG. 1 is a side view of a medical diagnostics installation constructed in accordance with the principles of the present invention.

FIG. 2 is a schematic block diagram of the signal reception components of the installation of FIG. 1.

DESCRIPTION OF THE PREFERRED EMBODIMENTS

A medical diagnostics installation constructed in accordance with the principles of the present invention is shown in FIG. 1. In the exemplary embodiment of FIG. 1, the installation is an x-ray diagnostics installation, however, it will be understood that the invention disclosed herein can be used in any type of medical installation.

The x-ray diagnostics installation 1 of FIG. 1 includes a patient support 2, which is adjustable along its longitudinal axis, and which can also be tilted around a horizontal axis 3. An imaging system, including an x-ray image intensifier 4 and an x-radiator 5, which can assume different positions, is provided for generating an image of an examination subject on the patient support 2. The imaging system is displaceable along the longitudinal axis of the patient support 2, and is tiltable around a horizontal axis 6. Various possible positions of the patient support 2 and of the imaging system are shown in dashed lines in FIG. 1.

The transmission of control instructions for setting the x-ray installation 1 ensues in wireless fashion by means of a control console 7, which rests on a pedestal 8, and can be removable therefrom. The control console 7 includes control elements 9 for entering control instructions, and an infrared transmitter 10 and an ultrasound transmitter 11. The control instructions are simultaneously encoded in and transmitted by infrared and ultrasound transmission via separate transmission paths to an infrared receiver 12 and to an ultrasound receiver 13 at the x-ray installation 1.

As shown in FIG. 2, the infrared receiver 12 and the ultrasound receiver 13 are connected to a signal recognition circuit 14, the output of which is connected to one or more controllable components at the x-ray installation 1. The recognition circuit 14 permits the execution of a control instruction only when the information simultaneously received by the infrared receiver 12 and by the ultrasound receiver 13 is identical. A highly reliable information transmission from the control console 7 to the x-ray installation 1 is thereby assured.

The invention has been described in the context of FIG. 1 with reference to a remotely controllable x-ray diagnostics installation for supporting and examining a patient. Other types of medical devices, for example x-ray generators, x-ray video systems or the like, can be remotely controlled in the manner disclosed herein by means of two different types of wireless transmission signals. For example, the exposure data for the x-ray generator can be set by an operating device manipulable separately therefrom by means of the wireless transmission of control instructions.

Although other modifications and changes may be suggested by those skilled in the art, it is the intention of the inventor to embody within the patent warranted hereon all changes and modifications as reasonably and properly come within the scope of his contribution to the art.

I claim as my invention:

1. A medical diagnostics installation comprising:

examination means for conducting a medical examination of a patient including at least one remotely controllable component, said remotely controllable component having means for receiving control instructions connected thereto;

control means for wirelessly remotely transmitting control instructions to said means for receiving, said control means including means for generating a first type of information-carrying signal in which said control instructions are encoded and means for generating a second type of information-carrying signal in which said control instructions are encoded, and means for simultaneously transmitting said first and second types of information carrying signals to said means for receiving; and recognition means, connected to said means for receiving, for permitting execution of a control instruction by said controllable component only when the instructions respectively received from said means for generating a first type of information-carrying signal and said means for generating a second type of information-carrying signal are identical.

2. A medical diagnostics installation as claimed in claim 1 wherein said means for generating a first type of information carrying signal is an infrared transmission signal generator and wherein said means for generating a second type of information-carrying signal is an ultrasound emission generator.

* * * * *